US006458886B1

(12) United States Patent
Nielsen et al.

(10) Patent No.: US 6,458,886 B1
(45) Date of Patent: Oct. 1, 2002

(54) PRESSURE SENSITIVE ADHESIVE COMPOSITION

(75) Inventors: Anders Christian Nielsen, Copenhagen (DK); Inger Mann Nielsen, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/647,938

(22) PCT Filed: Apr. 21, 1999

(86) PCT No.: PCT/DK99/00224

§ 371 (c)(1),
(2), (4) Date: Oct. 18, 2000

(87) PCT Pub. No.: WO99/54422

PCT Pub. Date: Oct. 28, 1999

(30) Foreign Application Priority Data

Apr. 21, 1998 (DK) .............................................. 0556/98

(51) Int. Cl.[7] .................................................. C08K 3/00
(52) U.S. Cl. ........................................ 524/526; 523/176
(58) Field of Search ........................... 523/176; 524/526

(56) References Cited

U.S. PATENT DOCUMENTS

| | | | |
|---|---|---|---|
| 3,339,546 A | 9/1967 | Chen | 128/156 |
| 3,419,006 A | 12/1968 | King | 128/268 |
| 3,972,328 A | 8/1976 | Chen | 128/156 |
| 4,231,369 A | 11/1980 | Sørensen et al. | 128/283 |
| 4,367,732 A | 1/1983 | Poulsen et al. | 128/156 |
| 4,538,603 A | 9/1985 | Pawelchak et al. | 128/156 |
| 4,551,490 A | 11/1985 | Doyle et al. | 524/22 |
| 4,552,138 A | 11/1985 | Hofeditz et al. | 128/156 |
| 4,867,748 A | 9/1989 | Samuelsen | 604/336 |
| 5,051,259 A | 9/1991 | Olsen et al. | 424/443 |
| 5,133,821 A | 7/1992 | Jensen | 156/245 |
| 5,439,963 A | 8/1995 | Korpman | 524/271 |
| 5,453,319 A | 9/1995 | Gobran | 428/355 |
| 5,492,943 A | 2/1996 | Stempel | 523/111 |
| 5,643,187 A | 7/1997 | Næstoft et al. | 602/43 |
| 5,714,225 A | 2/1998 | Hansen et al. | 428/114 |

FOREIGN PATENT DOCUMENTS

| | | |
|---|---|---|
| DK | 154747 | 4/1988 |
| EP | 0 264 299 | 4/1988 |
| EP | 0 272 149 | 6/1988 |
| EP | 0 641 369 | 3/1995 |
| GB | 1 280 631 | 7/1972 |
| GB | 1 586 182 | 3/1981 |
| WO | 88/06894 | 9/1988 |
| WO | 98/17329 | 4/1998 |
| WO | 98/53771 | 12/1998 |
| WO | 99/11728 | 3/1999 |

OTHER PUBLICATIONS

EP0415183; Mar. 6, 1991; Dr. Hanns Pietsch et al.; abstract.

Primary Examiner—Edward J. Cain
(74) Attorney, Agent, or Firm—Jacobson Holman, PLLC

(57) ABSTRACT

A pressure adhesive composition suitable for medical purposes comprising a blockcopolymer consisting of or having a major content of diblock copolymer, one or more water soluble or water swellable hydrocolloids and optionally a tackifier resin said composition comprising from 10 to 60% of the total composition of a blockcopolymer comprising a monoalkenyl arene component and a conjugated diene component having a proportion of three-block copolymer to diblock copolymer from 3:1 to 1:15, from 10 to 45% of the total composition of a tackifier resin and from 20 to 65% of the total composition of one or more water soluble or water swellable hydrocolloids shows improved adhesive properties for application on skin renders it possible to avoid the use of plasticizers normally used in connection with styrene copolymers in adhesives.

9 Claims, No Drawings

PRESSURE SENSITIVE ADHESIVE COMPOSITION

FIELD OF THE INVENTION

The present invention relates to pressure sensitive adhesive compositions suitable for various medical applications and especially suitable for use for adhesion to the skin. The adhesive composition may be used for securing ostomy appliances to the skin and for sealing around an ostomy, for securing wound dressings or wound drainage bandages to the skin, for securing devices for collecting urine to the skin, or for securing orthoses or prostheses to the skin. More specifically, this invention relates to adhesive compositions comprising a blockcopolymer having a major content of di-block copolymer, the use of such adhesive compositions for the preparation of a wound dressing or an adhesive wafer for an ostomy appliance, and to wound dressings or ostomy appliances comprising such adhesive composition.

BACKGROUND OF THE INVENTION

Various skin adhesive agents are used today for the above mentioned purposes.

A very widespread embodiment of skin adhesive agents comprises a self-adhesive elastomeric matrix, in which water-absorbing, swelling particles, the so-called hydrocolloids, are dispersed.

Adhesive compositions comprising hydrocolloids have been known for many years. U.S. Pat. No. 3,339,549 discloses a blend of a rubbery elastomer such as polyisobutylene and one or more water soluble or water swellable hydrocolioids such as a powdery mixture of pectin, gelatine and carboxymethylcellulose. The adhesive mass has a water-insoluble film applied to one surface. A composition of this type is available commercially from E.R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds.

One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the composition to lose its integrity opening for leaks and the barrier must be replaced more often than is desirable from a skin protection point of view, and very often, a residue remains on the skin, which in many cases is difficulty to remove.

A number of attempts have been made to improve the properties of adhesive compositions in order to overcome the above-mentioned drawbacks.

In a number of embodiments, styrene copolymers have been incorporated which is disclosed in a number of patent references.

Thus, U.S. Pat. No. 4,231,369 Sorensen et al. disclose an ostomy skin barrier consisting of a styrene copolymer having dispersed therein a water soluble hydrocolloid gum and a tackifier.

In U.S. Pat. No. 4,367,732 Poulsen et al. disclose an ostomy skin barrier consisting of a water soluble hydrocolloid dispersed in a continuous phase consisting of a styrene copolymer, a hydrocarbon tackifier, and a plasticizer, an antioxidant, and an oily extender.

U.S. Pat. No. 4,551,490 (Doyle et al.) discloses medical grade pressure sensitive adhesive compositions comprising a homogeneous mixture of 5–30% of one or more polyisobutylenes, 3–20% of one or more styrene radial or block type copolymers having a content of diblock copolymer below 20%, mineral oil, one or more water soluble hydrocolloid gums, and a tackifier. One or more water swellable cohesive strengthening agents, an antioxidant, and various other optional ingredients also may be included within the adhesive composition.

U.S. Pat. No. 5,492,943 discloses a pressure sensitive adhesive composition including a blend of two viscoelastic adhesive elastomers, specifically, high molecular weight polyisobutylene and a styrene block copolymer, which along with a plasticizer (preferably petrolatum) and a suitable tackifier and antioxidant, form a continuous phase in which hydrocolloids such as sodium carboxymethy-cellulose and pectin are dispersed. The adhesive compositions disclosed in U.S. Pat. No. 5,492,943 are stated to be used for wafers for adhering ostomy appliances to the skin and differ from known compositions by comprising styrene blockcopolymers having a higher content of diblock copolymer, completely avoiding the use of low molecular weight polyisobutylene and furthermore by preferably nor including gelatine.

WO 98/17329 discloses adhesive compositions comprising below 20% of styrene copolymer having a major content of diblock copolymer and furthermore comprising a tackifying liquid constituent.

Adhesives based on three-block styrene-isoprene-styrene (SIS) copolymers are highly elastic and show a very high degree of cohesion. Traditional SIS-based adhesives are all modified using a resin and plasticizer in order to obtain a suitable balance between the plastic and elastic properties in order to obtain satisfactory adhesiveness and, at the same time, sufficient plasticity which implies that the adhesive is able adapt to the structure and follow the movements of the skin without loosing the grip.

The properties of the adhesive may be adapted shifting the composition of the copolymer which traditionally has been effected by changing the amount and type of resin and plasticizer, respectively. The block copolymer typically has been constituted by a three-block copolymer (SIS) having a minor content of diblock copolymer (Originally a "contamination" due to non-perfect polymerisation or coupling).

Now the process of polymerisation may be controlled and copolymers having different contents of diblock component may be produced, even copolymers consisting of only diblock copolymers may be made.

It has now been found that when controlling the contents of diblock component it is possible to impart new properties to the adhesive composition rendering the adhesive plastic and more adhesive which properties hitherto only have been obtainable through modification using low-molecular resins and plasticizers.

It has surprisingly been found that when using a block-copolymer having a major content of di-block copolymer it is possible to prepare an adhesive composition for application on skin without having to rely on the addition of plasticizers normally used in connection with styrene copolymers in adhesive compositions.

Furthermore, it is possible to obtain, when using adhesives according to the invention, properties beyond those obtainable with adhesives of the state of the art.

BRIEF DESCRIPTION OF THE INVENTION

The invention relates to pressure sensitive adhesive compositions suitable for various medical applications and especially suitable for use for adhesion to the skin, the use of such adhesive compositions for the preparation of a wound dressing or an adhesive wafer for an ostomy appliance, and to wound dressings or ostomy appliances comprising such adhesive composition.

DETAILED DESCRIPTION OF THE INVENTION

The present invention relates to a pressure sensitive adhesive composition suitable for medical purposes comprising a blockcopolymer consisting of or having a major content of diblock copolymer, one or more water soluble or water swellable hydrocolloids and optionally a tackifier resin, said composition comprising from 10 to 60% of the total composition of a blockcopolymer comprising a monoalkenyl arene component and a conjugated diene component having a proportion of three-block copolymer to diblock copolymer from 3:1 to 1:15, from 10 to 45% of the total composition of a tackifier resin and from 20 to 65% of the total composition of one or more water soluble or water swellable hydrocolloids.

It has been found that by varying the contents of diblock copolymer fraction of the composition it is possible to tailor the properties of the adhesive without having to add plasticizers such as DOA which may migrate. Such migration is especially a potential problem for adhesives to be used for wound dressings being in direct contact with open wounds and may further deteriorate other materials in contact with the adhesive such as a backing layer or film on an ostomy appliance or wound dressing. Furthermore, the use of low molecular liquid constituents are avoided.

The properties may be varied from the more elastic properties of a traditional three-block-copolymer such as a SIS copolymer being suitable for preparation of wound dressings or wafers for adhering ostomy appliances to the skin to more plastic properties being suitable for e.g. pastes or adhesives for adhering devices for collecting urine or for mouldable adhesives for sealing around e.g. an ostomy.

The use of a diblock copolymer in adhesives to be used on human skin gives the following advantages: It is possible to increase the tack and peel without increasing the hardness of the adhesive composition, the plasticity and softness of the adhesive composition is increased, i.e. the adhesive is rendered more mouldable giving a better adaptation to the structure and movements of the skin and the three-dimensional swelling of the adhesive upon absorption of water is essentially eliminated.

Preferably such compositions comprise from 25 to 50% of the total composition of the blockcopolymer, from 15 to 30% of the total composition of a tackifier resin and from 25 to 55% of the total composition of one or more water soluble or water swellable hydrocolloids.

The blockcopolymer used in the adhesives according to the invention is preferably a blockcopolymer comprising a monoalkenyl arene component and a conjugated diene component. The monoalkenyl arene component is suitably styrene, and the conjugated diene component is suitably a butadiene such as isoprene or 1,3-butadiene.

The blockcopolymers to be used in the adhesives according to the invention may suitably be a combination of SIS and SI copolymers or SBS and SB copolymers. In one embodiment of the invention, the adhesive comprises only a diblock copolymer and no triblock copolymer giving rise to very soft and mouldable substantially non-memory, putty-like adhesives.

Compositions according to the invention having more plastic properties will normally have a high content of diblock copolymer. When mixing a copolymer of SIS having about 40% diblock contents with a substantially pure diblock copolymer, the proportion will typically vary from about 3:1 to about 1:15, more preferred from about 3:1 to about 1:6. Thus, compositions of the invention typically have a proportion of triblock copolymer to diblock copolymer of 3:1 to 1:15, more preferred for use as an adhesive for an ostomy appliance from 3:1 to 1:4, preferably from 3:1 to 1:3.

Furthermore, the properties of the polymer is depending on the molecular weight of the triblock and diblock components of the copolymer of the composition. The molecular weight of the triblock copolymer is typically in the range 150.000–300.000, and a diblock copolymer comprised in a commercial mixture typically has a molecular weight in the range 75.000–150.000. A pure diblock copolymer to be used according to the invention may typically have a molecular weight of from 20,000 to 300,000.

Adhesive compositions according to the invention for use as adhesive in wound dressings or ostomy appliances may suitably comprise from 10 to 30% of the total composition of a blockcopolymer having a major content of diblock copolymer, from 10 to 30% of the total composition of a tackifier resin and from 25 to 55% of the total composition of one or more water soluble or water swellable hydrocolloids, and, if desired, from 1 to 25% of a branched water-dispersible polyester regulating the absorbing properties of the adhesive.

Suitable hydrocolloids for incorporation in the adhesive compositions of the invention are selected from naturally occurring hydrocolloids, semisynthetic hydrocolloids and synthetic hydrocolloids.

More particularly, the hydrocolloids are preferably selected from guar gum, locust bean gum (LBG), pectin, alginates, gelatine, xanthan and/or gum karaya; cellulose derivatives (e.g. salts of carboxymethylcellulose such as sodium carboxymethylcellulose, methylcellulose and hydroxypropylmethylcellulose) and/or sodium starch glycolate and/or polyvinylalcohol and/or polyethylene glycol.

An optional tackifier resin increasing the adhesive properties of the composition in order to ensure a good contact between an appliance and the skin may be a hydrocarbon tackifier homogeneously distributed in the mass. The tackifier is preferably a terpene tackifier resin or a dicyclopentadiene tackifier resin. Especially preferred according to the invention as hydrocarbon tackifier resin are polymers and copolymers of dicyclopentadiene, alpha-pinene and/or beta-pinene.

The adhesive compositions of the invention may optionally comprise further components normally used in formulation of adhesive compositions such as pigments such as zinc oxide or titanium dioxide. The compositions of the invention may optionally comprise minor amounts of conventional plasticizers if special properties are desired.

For some purposes it is suitable also to include smaller amounts of a filler in the mass of the invention which may add to the cohesion and also contribute to the plasticity. Such filler may e.g. be any filler known per se for ostomy or wound care purposes such as talc, calcium carbonate, china clay, zinc oxide or the like. Such filler may constitute up to 3–20% by weight of the composition.

Still further, the masses according to the invention may optionally comprise further constituents such as emollients, disinfecting agents and/or bactericidal agents known per se for use for ostomy or wound care purposes.

In a second aspect, the invention relates to a wound dressing comprising as adhesive component a pressure sensitive adhesive composition suitable for medical purposes comprising a blockcopolymer having a major content of diblock copolymer, one or more water soluble or water swellable hydrocolloids and optionally a tackifier resin, said composition comprising from 10 to 60% of the total composition of a blockcopolymer comprising a monoalkenyl arene component and a conjugated diene component having a proportion of three-block copolymer to diblock copolymer from 3:1 to 1:15, from 10 to 45% of the total composition of a tackifier resin and from 20 to 65% of the total composition of one or more water soluble or water swellable hydrocolloids.

A wound dressing normally comprises a water impervious layer or film which may be of any suitable material known per se for use in the preparation of wound dressings e.g. a foam, a non-woven layer or a polyurethane, polyethylene, polyester or polyamide film. Using a layer or film having a low modulus will also allow an easy application during application, if desired.

A suitable material for use as a water impervious film is a polyurethane. A preferred low friction film material is disclosed in U.S. Pat. No. 5,643,187. A thickness of this film is below 20 microns, more preferred about 12–18 microns is preferred for use with dressings according to the invention, thus resulting in a significant decrease of the modulus, compared to a film that is normally used when preparing medical dressings.

The water impervious layer or film is preferably a low-friction flexible polymer film reducing the risk of unwanted stress in the area of e.g. a crack or wound impeding the healing of such injure on a very exposed site such as the tip of a finger or toe.

A dressing of the invention preferably has bevelled edges in order to reduce the risk of "rolling-up" the edge of the dressing reducing the wear-time and thus disturbing and prolonging the healing of cracks normally healing slowly on tips of fingers or toes due to physical stress. A bevelling may be carried out discontinuously or continuously in a manner known per se e.g. as disclosed in EP patent No. 0 264 299 or in U.S. Pat. No. 5,133,821.

A protective cover or release liner may for instance be siliconized paper. It does not need to have the same contour as the dressing, e.g. a number of dressings may be attached to a larger sheet of protective cover. The protective cover is not present during the use of the dressing of the invention and is therefore not an essential part of the invention. The protective cover may be removed before or during application of the dressing.

Furthermore, a dressing of the invention may comprise a "non touch" grip known per se for applying the dressing to the skin without touching the adhesive layer. Such a non-touch grip is not present after application of the dressing.

It is advantageous to provide a dressing or wound dressing of the invention with components for treatment or prophylaxis of formation of wounds and/or skin abnormalities, e.g. with emollients or an active constituent e.g. retinoids for treating or preventing formation of psoriasis, eczema, callous skin, corns, insect bites, acne or blisters. A dressing of the invention may also contain medicaments such as bacteriostatic or bactericide compounds, e.g. iodine, iodopovidone complexes, chloramine, chlorhexidine, silver salts, zinc or salts thereof, tissue-healing enhancing agents, e.g. RGD tripeptides and the like, enzymes for cleansing of wounds, e.g. pepsin, trypsin and the like, pain relieving agents, or agents having a cooling effect which is also considered an aspect of the invention.

A dressing according to the invention may be prepared by a manner known per se for the preparation of medical dressings by substituting the raw materials and it will be routine for the skilled in the art to adapt the process parameters to the actual materials.

In a third aspect, the invention relates to an ostomy appliance comprising an adhesive wafer comprising as adhesive component a pressure sensitive adhesive composition suitable for medical purposes comprising a blockcopolymer having a major content of diblock copolymer, one or more water soluble or water swellable hydrocolloids and optionally a tackifier resin, said composition comprising from 10 to 60% of the total composition of a blockcopolymer comprising a monoalkenyl arene component and a conjugated diene component having a proportion of three-block copolymer to diblock copolymer from 3:1 to 1:15, from 10 to 45% of the total composition of a tackifier resin and from 20 to 65% of the total composition of one or more water soluble or water swellable hydrocolloids.

An ostomy appliance of the invention may be in the form of a baseplate forming part of a two-piece appliance or in the form of a one-piece appliance comprising a collecting bag for collecting the material emerging from the stoma. A separate collecting bag may be attached to the baseplate by any manner known per se, e.g. through mechanical coupling using a coupling ring or through use of adhesive flanges.

An ostomy appliance of the invention also typically comprises a water impervious layer or film and a release liner as discussed above.

An ostomy appliance of the invention may be produced in a manner known per se from materials conventionally used for the preparation of ostomy appliances. In a preferred embodiment of an ostomy appliance of the invention, the adhesive plate for securing the appliance to the abdomen of the ostomate is of the kind comprising two different adhesives in the form of a roll of the kind disclosed in WO 89/05619. Such appliances may comprise two different adhesives according to the invention or one adhesive according to the invention and another skin-friendly adhesive, e.g. any skin-friendly adhesive known per se for ostomy purposes, e.g. an adhesive comprising hydrocolloids or other moisture absorbing constituents for prolonging the time of use. Such adhesive may suitably be of the type disclosed in GB patent specification No.1 280 631, in DK patent specifications Nos. 127,578, 148,408, 154,806, 147,226, 154,747 or 169,711, in EP published application Nos. 0 097 846 and 0 415 183, in SE published application No. 365,410, in WO publication No. 88/06894, in NO published application No. 157,686 or in U.S. Pat. Nos. 4,367,732 and 5,051,259. An ostomy appliance according to the invention may also be of the kind disclosed in WO 98/53771.

The invention is explained more in detail in the below examples disclosing embodiments thereof.

MATERIALS AND METHODS

LVSI 101 from Shell Chemical Company: Styrene-isoprene-styrene diblock copolymer (SI) having a molecular weight of about 30,000 as determined by GPC Kraton KX603 from Shell Chemical Company: A mixture of 60 w/w % Styrene-Isoprene-Styrene linear copolymer having Mn in the range 150.000–300.000, and 40% Styrene-Isoprene (SI) diblock copolymer having Mn in the range 75.000–150.000. The amount of styrene in the product is 15–16%

SolTe 9104 from ENICHEM: A mixture of 60 w/w % Styrene-Isoprene-Styrene branched copolymer having Mn in the range 150.000–300.000, and 40% Styrene-isoprene (SI) diblock copolymer having Mn in the range 75.000–150.000. The amount of styrene in the product is 15–16%

Arkon P70: A saturated alicyclic hydrocarbon resin from Arakawa Chemical Industries having a molecular weight of 610 and a softening point of 70° C.

Arkon P90: A saturated alicyclic hydrocarbon resin from Arakawa Chemical Industries having a molecular weight 570 and a softening point of 90° C.

Arkon P115: A saturated alicyclic hydrocarbon resin from Arakawa Chemical Industries having a molecular weight of 710 and a softening point of 115° C.

Regalite® R91: A fully hydrogenated resin from HERCULES Inc.

Foral 85: Foral 85-E, A hydrogenated Rosin from HERCULES Inc.

Dioctyladipate, plasticizer from International Speciality Chemicals Ltd. A.

Citrofol A1, plasicizer, triethyl citrate ester from Jungbunzlauer GmbH, Ladenburg, Germany Citrofol B2, plasicizer, acetyl-tributyl citrate ester from Jungbunzlauer GmbH, Ladenburg, Germany AQ1045 from Eastman. A branched water-dispersible polyester. Pectin: Pectin LM 12CG Z or Pectin USP/100 from Copenhagen Pectin A/S.

Natrosol: Hydroxyethylcellulose, Non-ionic, water soluble ethers of cellulose and ethylene oxide. Produced by AQUALON, a division of HERCULES Inc.

Paraffin oil: PL 500 from Parafluid Mineral Oel

CMC: Sodium carboxymethylcellulose available from Hercules under the trade name Blanose 9H4XF or from Akzo under the trade mark Akucell® AF2881

AquaSorb® A500: Crosslinked carboxymethylcellulose (CMC) from Aqualon, a Division of Hercules Incorporated.

Calcium alginate: Sorbalg PH470 from Danisco Ingredients, Denmark

A Z mixer Type LKB 025 from Herman-Linden was used.

EXPERIMENTAL PART

EXAMPLES 1–7

Adhesive compositions according to the invention having the compositions stated in the below Table 1 were produced in a high shear Z-blade type of mixer at 130° C. Initially the Kraton® KX603-component was added and when plastified, hen the LVSI-101 was added slowly in order to insure complete mixing of the components. After approx. 30 min. a homogenous mixture was obtained and all the resins were added slowly in order to ensure a thorough mixing. After further 15 min., optional plasticizers were added, and again mixing was continued until the mixture appears transparent. Finally, the mixing chamber was cooled to 90° C. and the hydrocolloid particles were added, and mixing is continued for another 20 min. under reduced pressure. The hot adhesive from the mixing chamber is moulded into 1 mm thickness between to sheets of silicone paper.

TABLE 1

| Ingredient | \multicolumn{7}{c}{Example} |
|---|---|---|---|---|---|---|---|
|  | 1 | 2 | 3 | 4 | 5 | 6 | 7 |
| LVSI 101 | 30 | 25 | 32 | 26.67 | 26.67 | 26.67 | 32 |
| Kraton ® KX603 | 5 | 5 | 6 | 5 | 5 | 5 | 8 |
| Arkon P90 | 15 | 20 | 20 | 16.67 | 16.67 | 16.67 | 20 |
| Pectin | 50 | 50 | 40 | 50 | 40 | 40 | 40 |
| Paraffin oil |  |  | 2 | 1.67 | 1.67 | 1.67 |  |
| Natrosol |  |  |  |  | 10 |  |  |
| CMC |  |  |  |  |  | 10 |  |

EXAMPLES 8–12

In an analogous method as described in Example 1 adhesive compositions according to the invention comprising SolTe® 9104 instead of Kraton® KX603 and having the compositions stated in the below Table 2 were produced.

TABLE 2

| Ingredient | \multicolumn{5}{c}{Example} |
|---|---|---|---|---|---|
|  | 8 | 9 | 10 | 11 | 12 |
| LVSI 101 | 10.3 | 10.3 | 10.3 | 10.3 | 6.8 |
| SolTe ® 9104 | 10.3 | 10.3 | 10.3 | 10.3 | 13.6 |
| Foral 85 | 14.0 | 15.4 | 20.0 | 20.0 | 20.0 |
| Arkon P70 | 25.6 | 15.4 | 19.6 | 10.6 | 19.6 |
| CMC | 8.0 |  | 8.0 | 8.0 | 8.0 |
| AquaSorp | 28.0 | 36.0 | 28.0 | 28.0 | 28.0 |
| AQ 1045 | 4.0 | 12.8 | 4.0 | 12.8 | 4.0 |

EXAMPLES 13–20

In an analogous method as described in Example 1 adhesive compositions according to the invention comprising SolTe® 9104 instead of Kraton® KX603 and having the compositions stated in the below Table 3 were produced.

TABLE 3

| Example | 13 | 14 | 15 | 16 | 17 | 18 | 19 | 20 |
|---|---|---|---|---|---|---|---|---|
| Ingredient |  |  |  |  |  |  |  |  |
| LVSI 101 | 6.8 | 12.8 | 10.7 | 8.5 | 10.7 | 6.8 | 6.0 | 8.5 |
| SolTe ® 9104 | 13.7 | 25.6 | 21.4 | 17.1 | 21.7 | 13.7 | 12.0 | 17.1 |
| Arkon P70 | 25.6 | 16.0 | 24.0 | 32.0 | 18.1 | 25.6 | 22.4 |  |
| Foral 85 | 5.1 | 9.6 | 8.0 | 6.4 | 13.8 | 5.1 | 4.5 | 6.4 |
| Regalite R91 |  |  |  |  |  |  |  | 32.0 |
| Calcium Alginate | 9.8 | 7.2 | 7.2 | 7.2 | 7.2 | 7.2 | 7.2 | 7.2 |
| Aquasorp | 39.0 | 28.8 | 28.8 | 28.8 | 28.8 | 28.8 | 28.8 | 28.8 |
| AQ 1045 |  |  |  |  |  | 12.8 | 19.1 |  |

EXAMPLES 21–23

In an analogous method as described in Example 1 adhesive compositions according to the invention having the compositions stated in the below Table 4 were produced.

TABLE 4

| Ingredient | Example | | |
|---|---|---|---|
| | 21 | 22 | 23 |
| Kraton KX603 | 10.1 | 6.7 | 6.70 |
| LVSI 101 | 29.95 | 21.40 | 21.40 |
| Arkon P70 | 29.95 | 23.40 | 23.40 |
| CMC | | 10.50 | |
| Pectin | | 38.00 | |
| Natrosol | 30.00 | | 48.50 |

EXAMPLES 24–27

In an analogous method as described in Example 1 adhesive compositions according to the invention having the compositions stated in the below Table 5 were produced.

TABLE 5

| Ingredient | Example | | | |
|---|---|---|---|---|
| | 24 | 25 | 26 | 27 |
| SolTe 9104 | 16.0 | 16.0 | 16.0 | 16.0 |
| LVSI-101 | 8.0 | 8.0 | 8.0 | 8.0 |
| Arkon P70 | 35.6 | | 35.6 | 35.6 |
| Arkon P115 | | 35.6 | | |
| DOA | 4.4 | 4.4 | | |
| Citrofol A1 | | | 4.4 | |
| Citrofol B2 | | | | 4.4 |
| Aquasorb A500 | 36.0 | 36.0 | 36.0 | 36.0 |

EXAMPLE 28

Test of adhesive properties of dressings comprising adhesives according to the invention as compared to commercial products.

The adhesives produced in Examples 9 and 14 were compared with DuoDerm from ConvaTec with respect to the relative areas of still being fixed to the skin after various times.

In total 20 healthy volunteers tested the commercial dressings and dressings produced in a similar manner comprising adhesive according to the invention. The products were sterilised.

10*10 cm dressings were placed on the back of the test persons and the relative areas still being in contact with the skin was evaluated at the beginning of the test and after 1, 2 and 3 days. The results are stated in the below Table 6.

TABLE 6

| Day | Product | Area in contact with skin (%) |
|---|---|---|
| 0 | Example 9 | 100 |
| 0 | Example 24 | 100 |
| 0 | DuoDerm | 100 |
| 1 | Example 9 | 93 |
| 1 | Example 24 | 99 |
| 1 | DuoDerm | 89 |
| 2 | Example 9 | 89 |
| 2 | Example 24 | 95 |
| 2 | DuoDerm | 80 |
| 3 | Example 9 | 89 |
| 3 | Example 24 | 95 |
| 3 | DuoDerm | 79 |

It appears from the above table that the area of contact of dressings comprising an adhesive according to the invention is larger than that of the commercial dressing DuoDerm over three days, comparable with the typical wear time of such a wound dressing.

What is claimed is:

1. A pressure sensitive adhesive composition suitable for medical purposes comprising from 10 to 60% of a block-copolymer with a monoalkenyl arene component and a conjugated diene component having a proportion of three-block copolymer to diblock copolymer from 3:1 to 1:15, from 10 to 45% of a tackifier resin and from 20 to 65% of one or more water soluble or water swellable hydrocolloids.

2. An adhesive composition as claimed in claim 1 wherein the proportion of three-block copolymer to diblock copolymer is from 3:1 to 1:4.

3. An adhesive composition as claimed in claim 2 wherein the proportion of three-block copolymer to diblock copolymer is from 3:1 to 1:3

4. An adhesive composition as claimed in claim 1 comprising a blockcopolymer consisting of a diblock copolymer and one or more water soluble or water swellable hydrocolloids.

5. An adhesive composition as claimed in claim 1 comprising from 25 to 50% of the total composition of the blockcopolymer, a from 10 to 30% of the total composition of a tackifier resin and from 25 to 55% of the total composition of one or more water soluble or water swellable hydrocolloids.

6. A wound dressing comprising as adhesive component a pressure sensitive adhesive composition suitable for medical purposes comprising a blockcopolymer comprising a monoalkenyl arene component and a conjugated diene component having a proportion of three-block copolymer to diblock copolymer from 3:1 to 1:15, one or more water soluble or water swellable hydrocolloids and optionally a tackifier resin.

7. An ostomy appliance comprising an adhesive wafer comprising a pressure sensitive adhesive composition suitable for medical purposes comprising a blockcopolymer comprising a monoalkenyl arene component and a conjugated diene component having a proportion of three-block copolymer to diblock copolymer from 3:1 to 1:15, one or more water soluble or water swellable hydrocolloids and optionally a tackifier resin.

8. A pressure sensitive adhesive composition suitable for medical purposes comprising from 10 to 60% of a block-copolymer with a monoalkenyl arene component and a conjugated diene component having a proportion of three-block copolymer to diblock copolymer from 3:1 to 1:15, from 15 to 45% of a tackifier resin and from 20 to 65% of one or more water soluble or water swellable hydrocolloids.

9. A pressure sensitive adhesive composition suitable for medical purposes comprising from 10 to 60% of a block-copolymer with a monoalkenyl arene component and a conjugated diene component having a proportion of three-block copolymer having a molecular weight in the range 150,000–300,000 to diblock copolymer having a molecular weight in the range 75,000–150,000 from 3:1 to 1:15, from 10 to 45% of a tackifier resin and from 20 to 65% of one or more water soluble or water swellable hydrocolloids.

* * * * *